United States Patent [19]

Murcin et al.

[11] Patent Number: 5,022,819
[45] Date of Patent: Jun. 11, 1991

[54] AIR FRAGRANCE DEVICE FOR CEILING

[76] Inventors: Daniel Murcin; Neva Murcin, both of 8800 66th St. N., Pinellas Park, Fla. 34666

[21] Appl. No.: 442,905

[22] Filed: Nov. 29, 1989

[51] Int. Cl.[5] ............................................. F01D 25/00
[52] U.S. Cl. ........................................ 416/62; 416/5
[58] Field of Search ............................ 416/62, 224, 5; 422/124, 306; 55/279

[56] References Cited

U.S. PATENT DOCUMENTS

| | | | |
|---|---|---|---|
| 4,422,824 | 12/1983 | Eisenhardt, Jr. | |
| 4,563,333 | 1/1986 | Frigon | |
| 4,604,114 | 8/1986 | Ward | 55/279 |
| 4,662,823 | 5/1987 | Cooke | 416/62 |
| 4,676,721 | 6/1987 | Hardee | |
| 4,753,573 | 6/1988 | McKnight | 416/62 |
| 4,840,650 | 6/1989 | Matherne | 416/62 |
| 4,889,543 | 12/1989 | Burt | 416/62 |

Primary Examiner—Edward K. Look
Assistant Examiner—James A. Larson
Attorney, Agent, or Firm—Leon Gilden

[57] ABSTRACT

An apparatus wherein a plurality of generally "U" shaped clips are securable to opposed, elongated lateral edges of a ceiling fan blade, and the brackets are securable together by spaced parallel coil springs to maintain the brackets to the ceiling fan blade, and an air freshener packet including a plurality of tubes are spaced apart a predetermined distance equal to a distance spaced apart by the springs received through respective ones of the tubes to secure the tubes and the packet to the ceiling fan blade. A modification of the instant invention includes the "U" shaped brackets securable together by opposed pairs of flexible straps including hook and loop fasteners mounted at terminal ends thereof, and a modified deodorizing packet includes a plurality of polymeric springs securable to spaced apertures of an underside of the packet to position the packet above an upper fan blade surface during securement by the straps of the device.

6 Claims, 4 Drawing Sheets

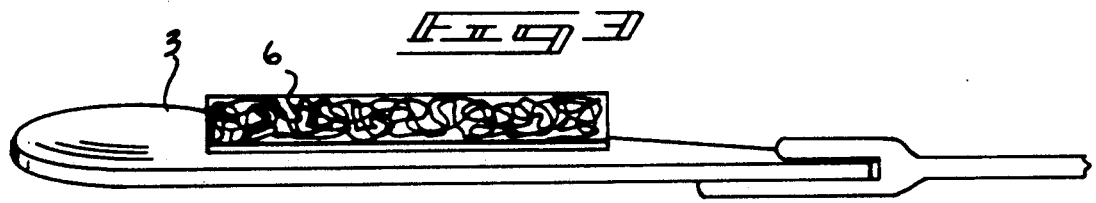
PRIOR ART
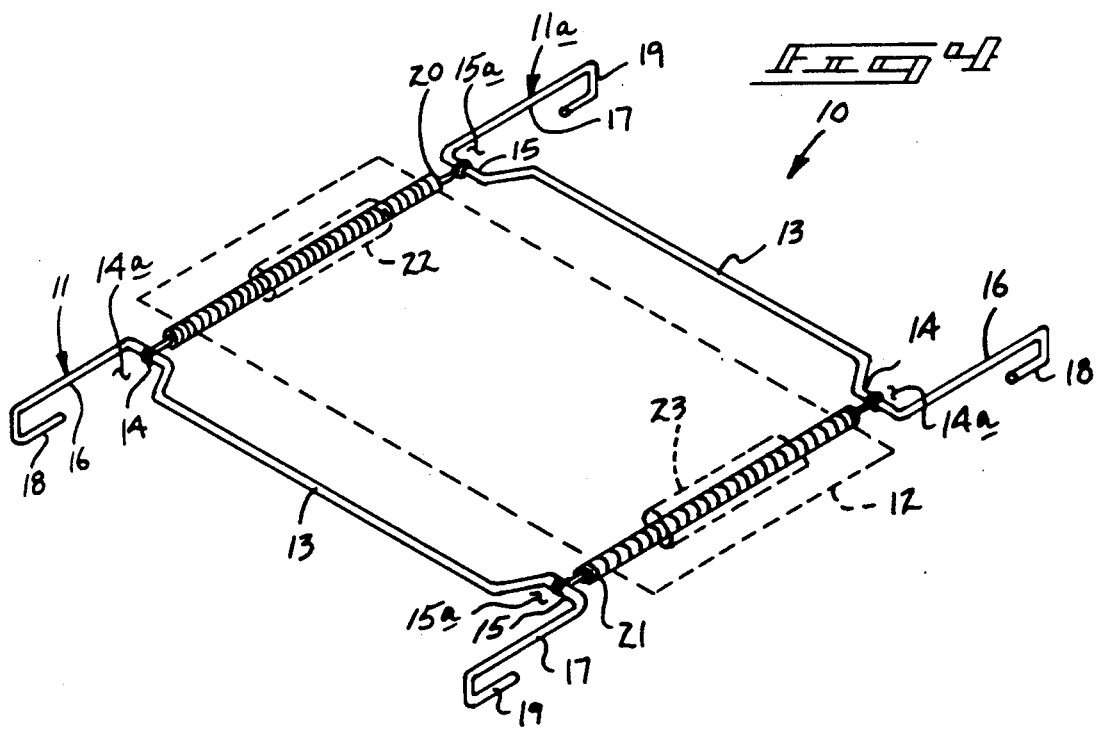

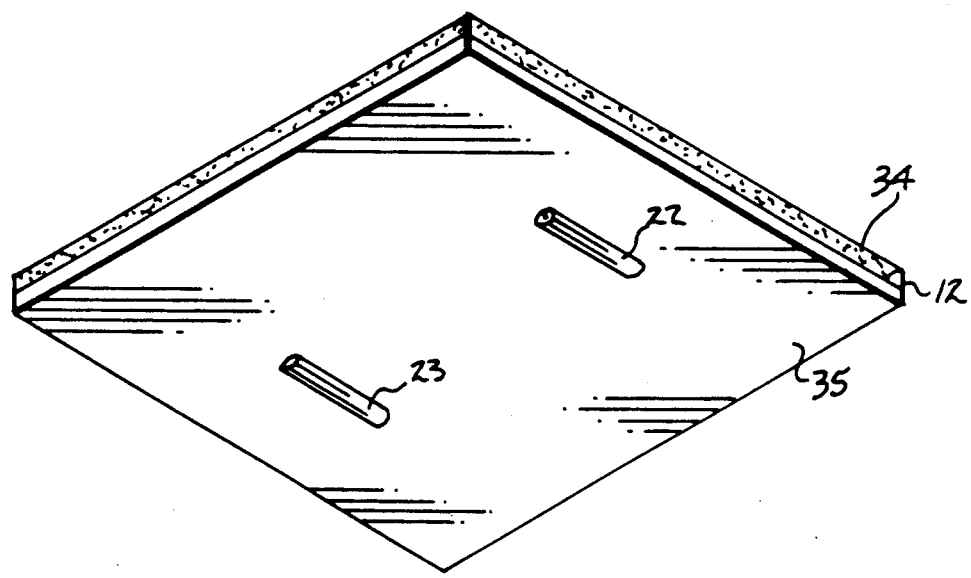
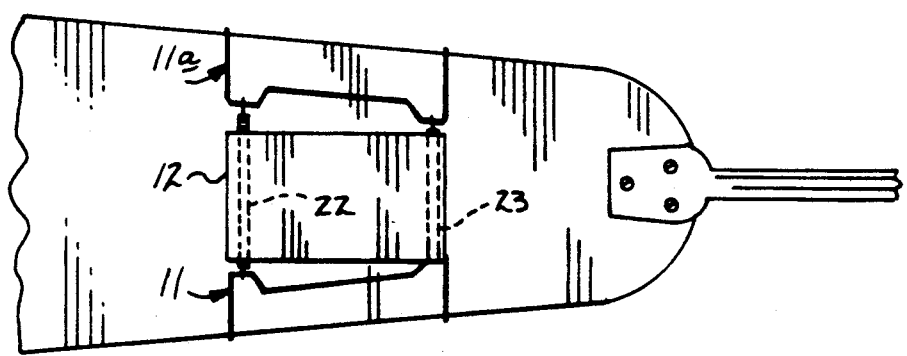

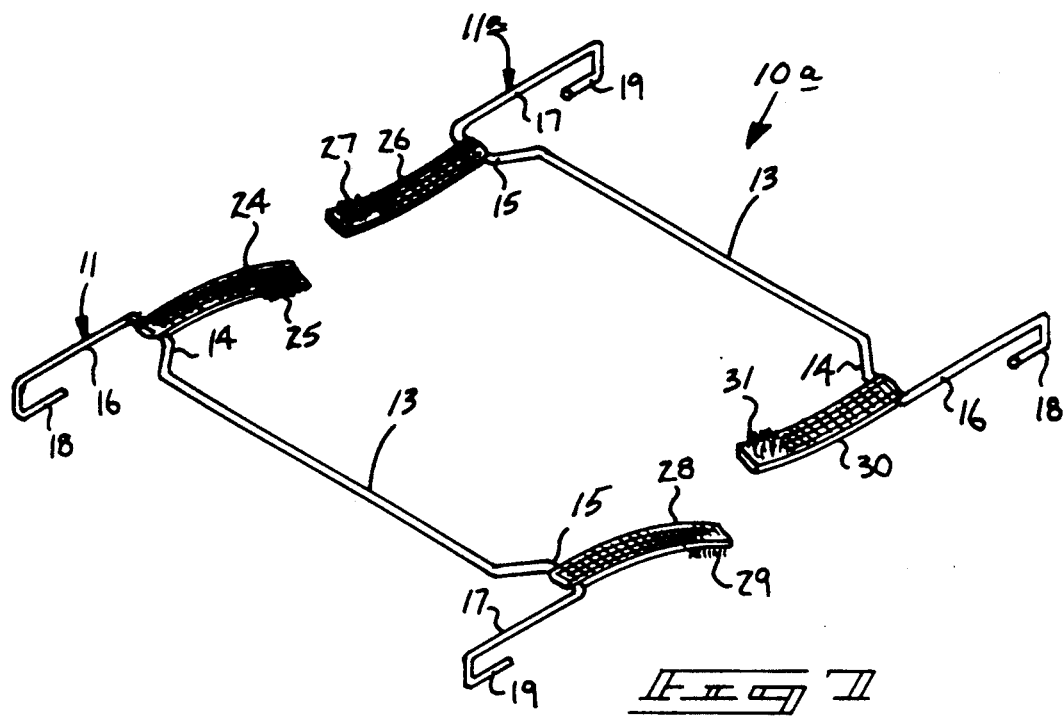
Fig 7
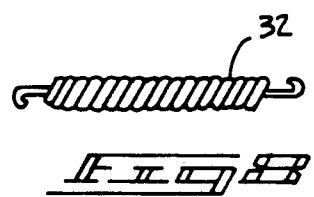
Fig 8
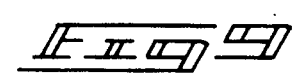
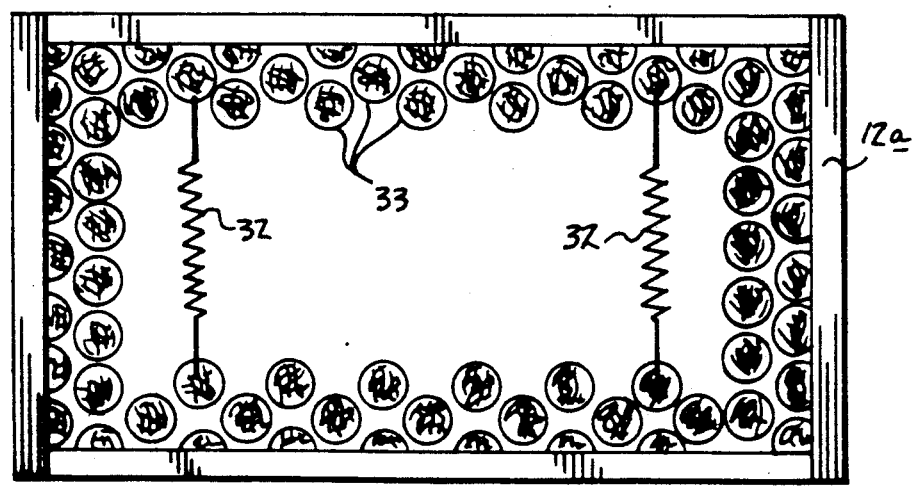
Fig 9

AIR FRAGRANCE DEVICE FOR CEILING

BACKGROUND OF THE INVENTION

1. Field of the Invention

The field of invention relates to an air freshening device, and more particularly pertains to a new and improved air fragrance device for ceiling fans to attach the device to a ceiling fan blade and thereby direct a fragrance throughout an associated area.

2. Description of the Prior Art

The use of filtration devices and fragrance devices and the like are known in the prior art. The prior art has heretofore provided various attachments for ceiling fan blades to enhance use of the fan blade during its circulatory motion in a particular room. Examples of the prior art include U.S. Pat. No. 4,676,721 to Hardee wherein a sock-like member is mounted overlying a fan blade of a ceiling fan to reduce dust and airborne debris from a room.

U.S. Pat. No. 4,604,114 to Ward sets forth an air filter construction provided with a fragrant scented material therewithin for utilization within conventional air delivery systems within a building.

U.S. Pat. No. 4,563,333 to Frigon sets forth a deodorizing fittting for use as an air filter for effective deodorizing of circulating air directed therethrough, wherein the device is mounted to a forward face of a conventional air filter.

U.S. Pat. No. 4,422,824 to Eisenhardt sets forth a fan blade construction of a ceiling fan formed with a central hollow cavity including filtration pads formed therethrough, as well as an ultra-violet germicidal light to destroy micro-organisms and bacteria contained within passing air.

U.S. Pat. No. 4,753,573 to McKnight sets forth an air filter for securement to a top or bottom surface of a fan blade of a circulating ceiling fan, wherein the filter includes an adhesive strip for securement of an edge of the filtration member to the fan blade.

As such, it may be appreciated that there is a continuing need for a new and improved air fragrance device for ceiling fans which addresses both the problems of effectiveness in construction and ease of use in providing a fragrance dispensing unit in cooperation with a ceiling fan.

SUMMARY OF THE INVENTION

In view of the foregoing disadvantages inherent in the known types of deodorizing units now present in the prior art, the present invention provides an air fragrance device for ceiling fans wherein the same is selectively securable to a top or bottom surface of an associated ceiling fan. As such, the general purpose of the present invention, which will be described subsequently in greater detail, is to provide a new and improved air fragrance device for ceiling fans which has all the advantages of the prior art air fragrance devices and none of the disadvantages.

To attain this, the air fragrance device for ceiling fans includes a plurality of generally "U" shaped clips securable to opposed, elongated lateral edges of a ceiling fan blade, wherein the brackets are securable together by spaced parallel coil springs to maintain the brackets to the ceiling fan blade, wherein an air freshener packet including a plurality of tubes are spaced apart a predetermined distance equal to a distance spaced apart by the springs received through respective ones of the tubes to secure the tubes and the packet to the ceiling fan blade. A modification of the instant invention includes the "U" shaped brackets securable together by opposed pairs of flexible straps including hook and loop fasteners mounted at terminal ends thereof, wherein a modified deodorizing packet includes a plurality of polymeric springs securable to spaced apertures of an underside of the packet to position the packet above an upper fan blade surface during securement by the straps of the device.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved air fragrance device for ceiling fans which has all the advantages of the prior art air fragrance devices and none of the disadvantages.

It is another object of the present invention to provide a new and improved air fragrance device for ceiling fans which may be easily and efficiently manufactured and marketed.

It is a further object of the present invention to provide a new and improved air fragrance device for ceiling fans which is of a durable and reliable construction.

An even further object of the present invention is to provide a new and improved air fragrance device for ceiling fans which is susceptible of a low cost of manufacture with regard to both materials and labor, and which accordingly is then susceptible of low prices of sale to the consuming public, thereby making such air fragrance devices for ceiling fans economically available to the buying public.

Still yet another object of the present invention is to provide a new and improved air fragrance device for ceiling fans which provides in the apparatuses and methods of the prior art some of the advantages thereof, while simultaneously overcoming some of the disadvantages normally associated therewith.

Still another object of the present invention is to provide a new and improved air fragrance device for ceiling fans wherein the same is selectively securable to a top or bottom surface of a ceiling fan and readily removable therefrom without abrasion or damage to the ceiling fan blade.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic side view taken in elevation of the device as illustrated in FIG. 2 illustrating the association of the filter and the ceiling fan blade structure.

FIG. 4 is an isometric illustration of the instant invention.

FIG. 5 is an isometric illustration of the fragrance dispensing package of the instant invention.

FIG. 6 is a top orthographic view of the instant invention in association with a ceiling fan blade.

FIG. 7 is an isometric illustration of a modified device utilized by the instant invention.

FIG. 8 is an orthographic view taken in elevation of a polymeric spring utilized by the modified device illustrated in FIG. 7.

FIG. 9 is a bottom orthographic view of the polymeric spring of FIG. 8 in association with a fragrance dispensing package utilized by the invention as illustrated in FIG. 7.

DESCRIPTION OF THE PREFERRED EMBODIMENT

Figure 1:
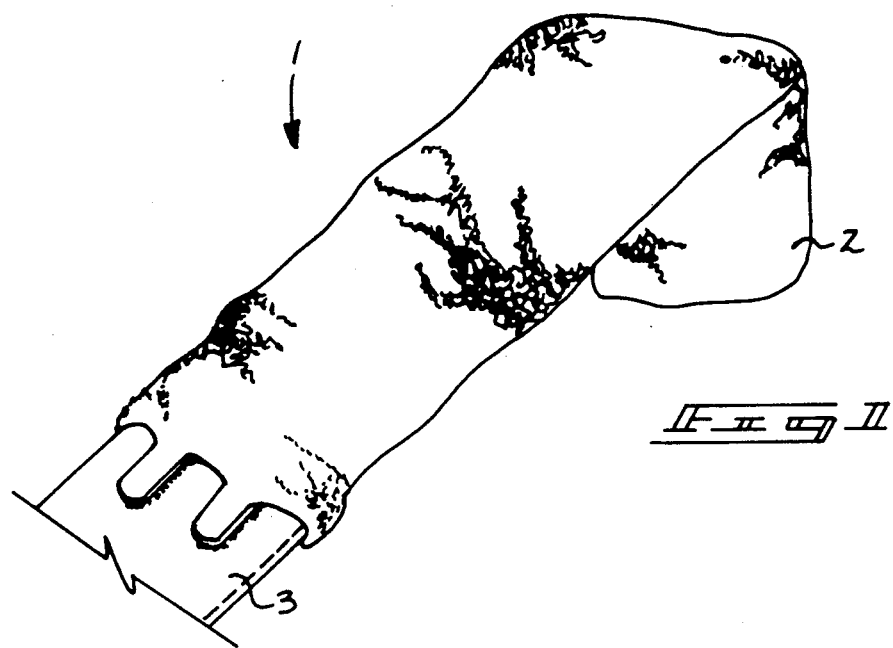
FIG. 1 is an isometric illustration of a prior art filtration type device for use with a ceiling fan.

With reference now to the drawings, and in particular to FIGS. 1 to 9 thereof, a new and improved air fragrance device for ceiling fans embodying the principles and concepts of the present invention and generally designated by the reference numerals 10 and 10a will be described.

Figure 2:
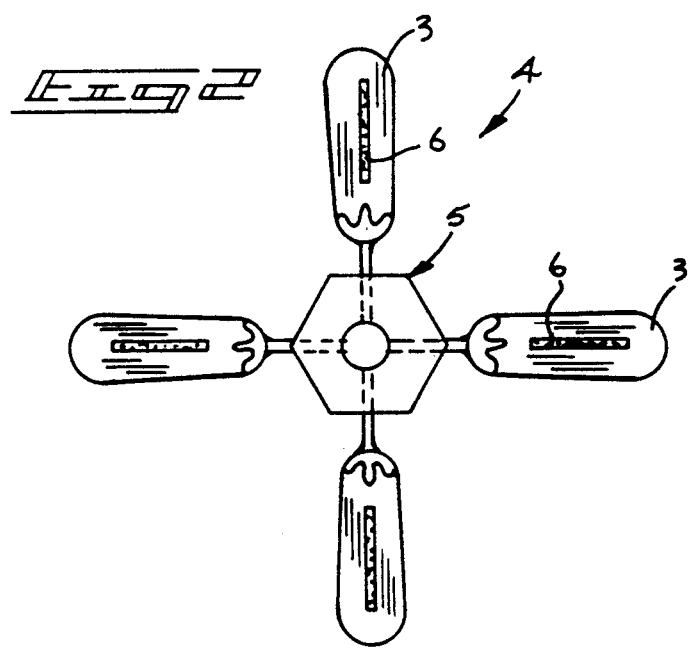
FIG. 2 is a top orthographic view of a further prior art air filtration device for use with a ceiling fan.

FIG. 1 illustrates a prior art ceiling fan device 1 wherein a sock-like member 2 is surmounted about a fan blade 3 of an associated ceiling fan. The member 2 includes fastening tabs at its open end to secure the member about an associated fan blade. The sock member 2 is formed of a generally open-weave type fabric to enable and effect a dust absorption procedure during rotation of the fan blade 3, with the sock member 2 mounted thereon. FIG. 2 illustrates a further modification air filtration type device 4 wherein a filter cartridge 6 is mounted to a fan blade 3 of a ceiling blade 5. The filtration member 6 is mounted generally orthogonally relative to a top or bottom surface of the fan blade 3 and during rotation of the fan blade directs relative motion of the filter 6 relative to airborne particles within the environment of the fan blade.

More specifically, the air fragrance device 10 of the instant invention essentially comprises a first "U" shaped clip member 11 cooperating with a second "U" shaped clip member 11a of a like configuration, but of mirror image positioning relative to the first "U" shaped clip member 11. Each clip member 11 and 11a includes an elongated axially aligned base rod 13 formed with a respective first and second "U" shaped securement end 14 and 15 oriented to form each terminal end of the base rod 13, with the open end of each "U" shaped securement end 14 and 15 facing forwardly of the base rod 13 and aligned with a respective first and second leg 16 and 17, wherein the first and second legs 16 and 17 are aligned parallel to one another and orthogonally oriented relative to the base rod 13 and are each an extension of a respective leg of each of the "U" shaped securement ends 14 and 15 that define a concave recess 14a and 15a. Each respective first and second legs 16 and 17 terminates in a respective first and second "U" shaped clip portion 18 and 19 that is offset ninety degrees relative to the plane defined by the base rod 13 and the first and second legs 16 and 17. A first coil spring 20 is formed with hook terminal ends securable to opposed first and second "U" shaped securement ends 14 and 15 of the respective first and second clip members 11 and 11a, with a second coil spring 21 formed with hooked end secured to opposed "U" shaped securement ends 15 and 14 of the respective first and second "U" shaped clips 11 and 11a. In use, the first and second "U" shaped clip portions 18 and 19 are surmounted about opposed lateral edges of a fan blade 3 and will overlie an air deodorizer package 12 formed with a solid air deodorizing agent therewithin, wherein rotation of the fan blade 3 of an associated fan 5 will impart the deodorizing agent from the package 3 throughout the environment of the fan.

The package 12 is formed with apertures or an overlying impregnated pad 34 to support the deodorizing agent mounted upon a rigid planar base 35. The planar base includes a bottom surface opposed to that upon which the laminated layer 34 surmounts and wherein the bottom surface of the base 35 includes spaced first and second tubes 22 and 23 to receive the respective springs 20 and 21 therethrough to secure the package 12 to the springs, as illustrated in FIG. 6 for example.

FIG. 7 illustrates a modified device 10a wherein the first and second "U" shaped clip members 11 and 11a are of identical construction to that defined within the air freshener device 10, as illustrated in FIG. 4, but in lieu of the first and second springs 20 and 21, opposed engageable strap members are utilized. Specifically, a first and second flexible strap 24 and 26 are secured to aligned and opposed first and second "U" shaped securement ends of the first and second "U" shaped clip members with a first and second respective hook and loop fastener patch 25 and 27 mounted upon respective bottom and top forward surface of each of the first and second strap members 24 and 26. A third and fourth respective flexible strap 28 and 30 are secured at rear terminal ends to respective second and first "U" shaped securement ends 15 and 14 that are aligned and integral to the respective first and second "U" shaped clip members 11 and 11a. The third and fourth straps 28 and 30 include respective third and fourth hook and loop fastener patches 29 and 31 fixedly mounted to respective bottom and top forward end surfaces of the straps 28 and 30. The aligned pairs of strap members are secured to one another to secure and maintain a modified air deodorize package 12a thereunder, wherein a polymeric spring 32 is utilized and secured to container apertures 33 formed throughout a bottom surface of the package 12a. Such a package may be found in U.S. Pat. No. 4,604,114 and incorporated herein by reference, wherein the polymeric springs 32 are thereafter added and secured to respective opposed apertures 33 and mounted to a surface of a fan blade to position the package 12a in a spaced relationship relative to a fan blade surface when the modified device 10a is mounted to the fan blade 3 in a manner to that as illustrated in FIG. 6 in the mounting of the device 10. In use, the circulatory motion of the associated fan blades 3 direct and dispense a fragrance impregnated within the packages 12 and 12a throughout an immediate environment.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An air fragrance device for securement to an elongate fan blade of a circulatory fan, wherein the blade includes an upper surface and a lower surface defining spaced first and second lateral edges, the device comprising, a first "U" shaped clip member securable to said first lateral edge, and a second "U" shaped clip member securable to said second lateral edge, and a fragrance impregnated package, and a first elongate securement means and a second elongate securement means, wherein the first and second elongate securement means are each spaced parallel to one another, and wherein each elongate securement means is joined to the first and second "U" shaped clip member at opposed terminal ends of each elongate securement means for securement of the package relative to the fan blade.

2. A device as set forth in claim 1 wherein each "U" shaped clip member comprises an elongate base rod, the base rod including a first "U" shaped securement end at a forward terminal end of each rod and a second "U" shaped securement end formed at a rear end of each rod, and a first leg directed forwardly of the first "U" shaped securement end, wherein the first leg is integrally formed to and orthogonally oriented relative to the first "U" shaped securement end, and a second leg directed orthogonally relative to the second "U" shaped securement end and oriented orthogonally relative thereto, wherein the first leg and second leg are aligned parallel relative to one another, and wherein the first leg, second leg, first "U" shaped securement end, second "U" shaped securement end, and base rod define a single plane, and a first "U" shaped clip portion integrally formed to a forward end of the first leg and a second "U" shaped clip portion to the forward end of the second leg of each "U" shaped clip member, wherein the first and second "U" shaped clip portions are rotated ninety degrees relative to the plane.

3. A device as set forth in claim 2 wherein the first and second "U" shaped clip members are arranged in a mirror image relationship relative to one another.

4. A device as set forth in claim 3 wherein the first and second elongate securement means comprises a respective first and second elongate coil spring spaced apart a predetermined distance.

5. A device as set forth in claim 4 wherein the package includes a first tube and a second tube, the first tube and second tube integrally mounted to a bottom surface of the package and aligned parallel to one another and spaced apart the predetermined distance, the first tube and second tube positioned for slidably receiving the respective first coil spring and second coil spring therethrough.

6. A device as set forth in claim 3 wherein the first elongate securement means is defined by a first flexible strip secured at its rearwardmost end to the first "U" shaped securement end of the first "U" shaped clip member, and a second flexible strip secured at its rear terminal end to the second "U" shaped end of the second clip member, and the first and second flexible strips include a hook and loop fastener patch mounted at a forward end of each first and second strips, and the second elongate securement means comprises a third flexible strip secured to the second "U" shaped securement end of the first "U" shaped clip member, and a fourth flexible strip secured at its rear terminal end to the first "U" shaped securement end of the second clip member, and the third and fourth flexible strips include respective hook and loop fastener patches formed at forward end portions of each respective third and fourth flexible strips.

* * * * *